United States Patent [19]

Maubru

[11] Patent Number: 5,620,484
[45] Date of Patent: Apr. 15, 1997

[54] COMPOSITIONS AND PROCESSES FOR DYEING KERATIN FIBRES WITH 6-HYDROXYINDOLINE AND OXIDATION BASES AT ACID PH'S

[75] Inventor: Mireille Maubru, Chatou, France

[73] Assignee: L'Oreal, Paris, France

[21] Appl. No.: 607,722

[22] Filed: Feb. 27, 1996

[30] Foreign Application Priority Data

Feb. 27, 1995 [FR] France ................... 95 02273

[51] Int. Cl.$^6$ ............................................. A61K 7/13
[52] U.S. Cl. ..................... 8/409; 8/406; 8/408; 8/410; 8/416; 8/421; 8/423
[58] Field of Search ................. 8/406, 408, 409, 8/410, 416, 421, 423

[56] References Cited

U.S. PATENT DOCUMENTS

| | | |
|---|---|---|
| 3,649,160 | 3/1972 | Kalopissis et al. ............ 8/409 |
| 4,013,404 | 3/1977 | Parent et al. .................. 8/423 |
| 5,061,289 | 10/1991 | Clausen et al. ............... 8/406 |
| 5,131,911 | 7/1992 | Lang et al. .................... 8/406 |
| 5,207,798 | 5/1993 | Cotteret et al. .............. 8/408 |
| 5,354,870 | 10/1994 | Lang et al. ................. 548/469 |
| 5,380,340 | 1/1995 | Neunhoeffer et al. ........ 8/409 |
| 5,391,206 | 2/1995 | Cotteret ....................... 8/408 |

FOREIGN PATENT DOCUMENTS

| | | |
|---|---|---|
| 0375977 | 7/1990 | European Pat. Off. . |
| 0428441 | 5/1991 | European Pat. Off. . |
| 0446132 | 9/1991 | European Pat. Off. . |
| 0465339 | 1/1992 | European Pat. Off. . |
| 0465340 | 1/1992 | European Pat. Off. . |
| 0634164 | 1/1995 | European Pat. Off. . |
| 1916139 | 11/1969 | Germany . |
| 3031709 | 4/1982 | Germany . |
| 3743769 | 7/1989 | Germany . |
| 3930446 | 3/1990 | Germany . |
| 4133957 | 4/1993 | Germany . |
| 1217479 | 12/1970 | United Kingdom . |
| 2180215 | 3/1987 | United Kingdom . |
| WO-A-9309759 | 5/1993 | WIPO . |
| WO-A-9408970 | 4/1994 | WIPO . |

OTHER PUBLICATIONS

English Derwent Abstract of DE-A-3743769, Jul. 1989.
English Derwent Abstract of DE-A-3031709, Apr. 1982.
English Derwent Abstract of EP-A-0634164, Jan. 1995.
English Derwent Abstract of EP-A-0428441, May 1991.
English Derwent Abstract of EP-A-0465339, Jan. 1992.
English Derwent Abstract of WO-A-9408970, Apr. 1994.

*Primary Examiner*—Paul Lieberman
*Assistant Examiner*—Caroline L. Dusheck
*Attorney, Agent, or Firm*—Finnegan, Henderson, Farabow, Garrett & Dunner, L.L.P.

[57] ABSTRACT

A ready-to-use composition for the oxidation dyeing of keratin fibers, in particular human keratin fibers such as the hair, comprising, in an acidic medium (pH<7), at least one oxidation base in combination with at least one coupler selected from 6-hydroxyindoline and acid addition salts thereof and an oxidizing agent, as well as to the dyeing process using this composition.

24 Claims, No Drawings

COMPOSITIONS AND PROCESSES FOR DYEING KERATIN FIBRES WITH 6-HYDROXYINDOLINE AND OXIDATION BASES AT ACID PH'S

The present invention is directed to a ready-to-use composition for the oxidation dyeing of keratin fibres, in particular human keratin fibres such as the hair, comprising, in an acidic medium, i.e., having a pH<7, at least one oxidation base in combination with 6-hydroxyindoline as a coupler and an oxidizing agent, as well as to the dyeing process using this composition.

It is known to dye keratin fibres, and in particular human hair, with dye compositions containing oxidation dye precursors, in particular ortho- or para-phenylenediamines and ortho- or para-aminophenols, which are generally referred to as oxidation bases. The oxidation dye precursors, or oxidation bases, are colorless or weakly colored compounds which, when combined with oxidizing products, may give rise to colored compounds and dyes by a process of oxidative condensation.

It is also known that the shades obtained with these oxidation bases may be varied by combining them with couplers or coloration modifiers, the latter being chosen in particular from aromatic meta-diamines, meta-aminophenols, meta-diphenols and certain indole or indoline compounds.

The variety of molecules used as oxidation bases and couplers makes it possible to obtain a wide range of colors.

The so-called "permanent" coloration obtained by means of these oxidation dyes must moreover satisfy a certain number of requirements. Thus, the dyes must have no toxicological drawbacks and must allow shades of the desired strength to be obtained and have good resistance to external agents, such as light, inclement weather, washing, permanent waving, perspiration and friction.

The dyes must also allow white hairs to be covered and, lastly, they must be as unselective as possible, that is to say they must allow the smallest possible differences in coloration, i.e., low selectivity, to be produced over the entire length of the same keratin fibre, which may indeed be differently sensitized, i.e., damaged between its tip and its root. In other words, it is desired to have dyes which produce coloration of low selectivity.

The oxidation dyeing of keratin fibres is generally performed in alkaline medium. However, alkaline media have the disadvantage of causing an appreciable amount of damage to the fibres. By way of example, compositions for the oxidation dyeing of keratin fibres in alkaline medium comprising at least one oxidation base and at least one indole derivative as a coupler have already been proposed in French patent application FR 2,008,797, the disclosure of which is incorporated herein by reference.

The oxidation dyeing of keratin fibres may also be performed acidic medium, in order to limit the degradation of the keratin fibres. However, the colorations obtained under these conditions are, unfortunately, generally less intense and not as fast as those obtained in alkaline medium.

Now, the inventor has discovered that it is possible to obtain novel dyes in acidic medium, which are capable of giving rise to (for an equivalent composition) more powerful colorations than the colorations of the prior art obtained at basic pH, and which are quite unselective, i.e., have low selectivity, and resistant to the various attacking factors to which the hair may be subjected, by combining at least one oxidation base, 6-hydroxyindoline or an acid addition salt thereof as a coupler and an oxidizing agent in a manner such that the resulting ready-to-use mixture has a pH of less than 7.

This discovery forms the basis of the present invention.

The first subject of the present invention is thus a ready-to-use composition for the oxidation dyeing of keratin fibres, and in particular human keratin fibres such as the hair, characterized in that it comprises, in a medium which is suitable for dyeing:

at least one oxidation base, 6-hydroxyindoline and/or at least one of the acid addition salts thereof as a coupler, and at least one oxidizing agent, the pH of this ready-to-use composition being less than 7.

The colorations obtained with the ready-to-use dye compositions in accordance with the invention are more intense than those of the prior art obtained with the same compositions used at basic pH, and moreover have low selectivity and excellent properties of resistance both to atmospheric agents such as light and inclement weather and to perspiration and the various treatments to which the hair may be subjected, e.g., washing and permanent waving.

Another subject of the invention is a process for the oxidation dyeing of keratin fibres using this ready-to-use dye composition.

The oxidation bases which may be used in the ready-to-use compositions in accordance with the invention are preferably chosen from para-phenylenediamines, bis(phenyl)alkylenediamines, para-aminophenols, ortho-aminophenols and heterocyclic bases, and the acid addition salts thereof.

The acid addition salts which may be used in the context of the dye compositions of the invention (oxidation bases and 6-hydroxyindoline) are chosen in particular from hydrochlorides, hydrobromides, sulphates and tartrates.

Among the para-phenylenediamines which may be used as oxidation bases in the context of the ready-to-use compositions in accordance with the invention, mention may preferably be made of the compounds corresponding to formula (I), and the acid addition salts thereof:

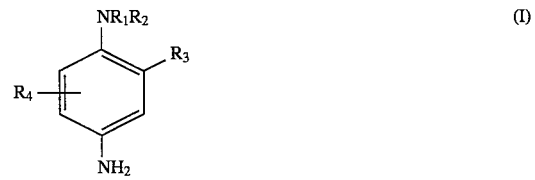

in which:

$R_1$ represents a hydrogen atom or a $C_1$–$C_4$ alkyl, $C_1$–$C_4$ monohydroxyalkyl, $C_2$–$C_4$ polyhydroxyalkyl, ($C_1$–$C_4$)alkoxy($C_1$–$C_4$)alkyl, phenyl or 4'-aminophenyl radical, $R_2$ represents a hydrogen atom or a $C_1$–$C_4$ alkyl, $C_1$–$C_4$ monohydroxyalkyl or $C_2$–$C_4$ polyhydroxyalkyl radical, $R_3$ represents a hydrogen atom, a halogen atom such as a chlorine, bromine, iodine or fluorine atom, or a $C_1$–$C_4$ alkyl, $C_1$–$C_4$ monohydroxyalkyl or $C_1$–$C_4$ hydroxyalkoxy radical, and $R_4$ represents a hydrogen atom or a $C_1$–$C_4$ alkyl radical.

Among the para-phenylenediamines of above formula (I) which may more preferably be mentioned are para-phenylenediamine, para-toluylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-amino-N,N-bis(β-hydroxyethyl)-3-methylaniline, 4-amino-3-chloro-N,N-bis(β-hydroxyethyl)aniline, 4-amino-N-(β-methoxyethyl)aniline, 2-β-hydroxyethyl-para-phenylenediamine, 2-fluoro-para-phenylenediamine, 2-isopropyl-para-phenylenediamine, 2-n-propyl-para-phenylenediamine, N-(β-hydroxypropyl)-para-phenylenediamine, 2-hydroxymethyl-para-phenylenediamine, N,N-dimethyl-3-methyl-para-phenylenediamine, N-(ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine and 2-β-hydroxyethyloxy-para-phenylenediamine, and the acid addition salts thereof.

Among the para-phenylenediamines of above formula (I) which are most preferred are para-phenylenediamine, para-toluylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 4-amino-N-(β-methoxyethyl)aniline and 2-chloro-para-phenylenediamine, and the acid addition salts thereof.

Among the bis(phenyl)alkylenediamines which may be used as oxidation bases in the context of the ready-to-use compositions in accordance with the invention, mention may preferably be made of the compounds corresponding to formula (II), and the acid addition salts thereof:

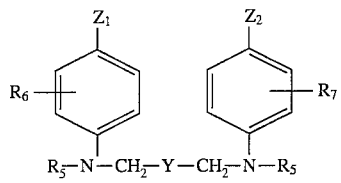

in which:

$Z_1$ and $Z_2$, which may be identical or different, represent a hydroxyl radical or a $NHR_8$ radical in which $R_8$ represents a hydrogen atom or a $C_1$–$C_4$ alkyl radical, $R_5$ independently represents a hydrogen atom or a $C_1$–$C_4$ alkyl, $C_1$–$C_4$ monohydroxyalkyl or $C_2$–$C_4$ polyhydroxyalkyl radical or a $C_1$–$C_4$ aminoalkyl radical in which the amino residue may be substituted, $R_6$ and $R_7$, which may be identical or different, represent a hydrogen of halogen atom or a $C_1$–$C_4$ alkyl radical, Y represents a radical, the radical being
—$(CH_2)_n$—; —$(CH_2)_m$—O—$(CH_2)_m$;
—$(CH_2)_m$—CHOH—$(CH_2)_m$— or $$-(CH_2)_{\overline{m}}-\underset{\underset{CH_3}{|}}{N}-(CH_2)_{\overline{m}}-;$$

in which n is an integer ranging from 0 to 8 inclusively and m is independently an integer ranging from 0 to 4 inclusively.

Among the bis(phenyl)alkylenediamines of above formula (II) which may more preferably be mentioned are N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine and N,N'-bis(ethyl)-N,N'-bis(4'-amino-3'-methylphenyl)ethylenediamine, and the addition acid salts thereof.

Among these bis(phenyl)alkylenediamines of formula (II), N,N'-bis(β-hydroxyethyl)-N,N'-bis(4'-aminophenyl)-1,3-diaminopropanol or one of the acid addition salts thereof is particularly preferred.

Among the para-aminophenols which may be used as oxidation bases in the context of the ready-to-use compositions in accordance with the invention, mention may preferably be made of the compounds corresponding to formula (III), and the acid addition salts thereof:

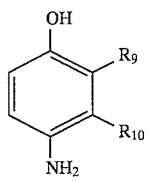

in which:

$R_9$ represents a hydrogen atom or a $C_1$–$C_4$ alkyl, $C_1$–$C_4$ monohydroxyalkyl, $(C_1$–$C_4)$alkoxy$(C_1$–$C_4)$alkyl or $C_1$–$C_4$ aminoalkyl radical, and $R_{10}$ represents a hydrogen or fluorine atom or a $C_1$–$C_4$ alkyl, $C_1$–$C_4$ monohydroxyalkyl, $C_2$–$C_4$ polyhydroxyalkyl, $C_1$–$C_4$ aminoalkyl, $C_1$–$C_4$ cyanoalkyl or $(C_1$–$C_4)$alkoxy$(C_1$–$C_4)$alkyl radical, it being understood that at least one of the radicals $R_9$ or $R_{10}$ represents a hydrogen atom.

Among the para-aminophenols of above formula (III) which may more preferably be mentioned are para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol and 4-amino-2-(β-hydroxyethylaminomethyl)phenol and the acid addition salts thereof.

Among the ortho-aminophenols which may be used as oxidation bases in the context of the ready-to-use compositions in accordance with the invention, mention may preferably be made of 2-aminophenol, 2-amino-5-methylphenol, 2-amino-6-methylphenol and 5-acetamido-2-aminophenol, and the acid addition salts thereof.

Among the heterocyclic bases which may be used as oxidation bases in the context of the ready-to-use compositions in accordance with the invention, mention may preferably be made of pyridine derivatives, pyrimidine derivatives, pyrazole derivatives and the acid addition salts thereof.

Among the pyridine derivatives which may preferably be mentioned are the compounds described, for example, in Great Britain patents 1,026,978 and 1,153,196, the disclosures of which are incorporated herein by reference, such as 2,5-diaminopyridine and the acid addition salts thereof.

Among the pyrimidine derivatives which may preferably be mentioned are the compounds described, for example, in German patent DE 2,359,399 or Japanese patents JP 88-169,571 and JP 91-333,495, the disclosures of which are incorporated herein by reference, such as 2,4,5,6-tetraaminopyrimidine, 4-hydroxy-2,5,6-triaminopyrimidine and the acid addition salts thereof.

Among the pyrazole derivatives which may preferably be mentioned are the compounds described in German patents DE 3,843,892 and DE 4,133,957 and patent applications WO 94/08969 and WO 94/08970, the disclosures of all of which are incorporated herein by reference, such as 4,5-diamino-1-methylpyrazole, 3,4-diaminopyrazole and the acid addition salts thereof.

The oxidation base or bases preferably represent approximately from 0.0005 to 12% by weight relative to the total weight of the dye composition, and even more preferably approximately from 0.005 to 6% by weight.

The 6-hydroxyindoline and/or the acid addition salts thereof preferably represent(s) approximately from 0.0005 to 5% by weight relative to the total weight of the dye composition, and even more preferably approximately from 0.005 to 3% by weight.

According to an essential characteristic of the present invention, the pH of the ready-to-use dye composition in accordance with the invention is less than 7 and may preferably vary from 3 to 6.9. The pH may be adjusted to the desired value using acidifying or optionally basifying agents usually used in the dyeing of keratin fibres.

Among the acidifying agents which may be mentioned, by way of example, are inorganic or organic acids such as hydrochloric acid, orthophosphoric acid, carboxylic acids such as tartaric acid, citric acid and lactic acid, and sulphonic acids.

Among the basifying agents which may be mentioned, by way of example, are aqueous ammonia, alkaline carbonates, alkanolamines such as mono-, di- and triethanolamines and derivatives thereof, sodium hydroxide, potassium hydroxide and the compounds of formula (IV):

in which R is a propylene residue optionally substituted with a hydroxyl group or a $C_1$–$C_4$ alkyl radical; $R_{11}$, $R_{12}$, $R_{13}$ and $R_{14}$, which may be identical or different, represent a hydrogen atom or a $C_1$–$C_4$ alkyl or $C_1$–$C_4$ hydroxyalkyl radical.

The oxidizing agent present in the ready-to-use dye composition in accordance with the invention may be chosen from the oxidizing agents conventionally used in oxidation dyeing and preferably from hydrogen peroxide, urea peroxide, alkali metal bromates and persalts such as perborates and persulphates. Hydrogen peroxide is particularly preferred.

In addition to the dyes defined above, the ready-to-use dye composition in accordance with the invention may also contain other couplers and/or direct dyes in order to modify the shades or to enrich them with glints.

The medium which is suitable for dyeing (or the support) in the dye compositions generally comprises water or a mixture of water and at least one organic solvent to solubilize the compounds which would not be sufficiently soluble in water. Organic solvents which may be mentioned, for example, are $C_1$–$C_4$ lower alkanols such as ethanol and isopropanol; glycerol; glycols and glycol ethers such as 2-butoxyethanol, propylene glycol, propylene glycol monomethyl ether, diethylene glycol monomethyl ether and monoethyl ether, as well as aromatic alcohols such as benzyl alcohol or phenoxyethanol, similar products and mixtures thereof.

The solvents may be present in proportions preferably ranging approximately from 1 to 40% by weight relative to the total weight of the dye composition, and even more preferably ranging approximately from 5 to 30% by weight.

The ready-to-use dye compositions in accordance with the invention may also include various adjuvants used conventionally in compositions for dyeing the hair, such as anionic, cationic, nonionic, amphoteric or zwitterionic surfactants or mixtures thereof, anionic, cationic, nonionic, amphoteric or zwitterionic polymers or mixtures thereof, inorganic or organic thickeners, antioxidants, penetration agents, sequestering agents, fragrances, buffers, dispersing agents, conditioners, film-forming agents, preserving agents and opacifying agents.

A person skilled in the art will take care to choose this or these optional complementary compound(s) such that the advantageous properties intrinsically associated with the ready-to-use composition in accordance with the invention are not, or are substantially not, adversely affected by the addition or additions envisaged.

The ready-to-use dye compositions in accordance with the invention may be in various forms, such as in the form of liquids, creams, gels or any other form which is suitable for dyeing keratin fibres, and in particular human hair.

Another subject of the invention is a process for dyeing keratin fibres, and in particular human keratin fibres such as the hair, using the ready-to-use dye composition as defined above.

According to this process, at least one ready-to-use dye composition as defined above is applied to the fibres and is left in place from 3 to 50 minutes approximately, preferably from 5 to 30 minutes approximately, after which the hair is rinsed, optionally washed with shampoo, rinsed again and dried.

According to a preferred embodiment, the process includes a preliminary step comprising separately storing, on the one hand, a composition (A) comprising, in a medium which is suitable for dyeing, at least one oxidation base and 6-hydroxyindoline and/or at least one of the acid addition salts thereof and, on the other hand, a composition (B) including, in a medium which is suitable for dyeing, at least one oxidizing agent as defined above, and in mixing them together, at the time of use, before applying this mixture to the keratin fibres, the pH of the compositions (A) and (B) being such that after mixing from 10 to 90% of the composition (A) with 90 to 10% of the composition (B), the pH of the resulting mixture is less than 7.

The pH of the compositions (A) and (B) may be adjusted to the desired value using conventional acidifying or optionally basifying agents as defined above.

Another subject of the invention is a multi-compartment device or dyeing kit or any other multi-compartment packaging system, a first compartment of which contains composition (A) as defined above and a second compartment of which contains the oxidizing composition (B) as defined above. These devices may be equipped with a means which makes it possible to deliver the desired mixture onto the hair, such as the devices described in French patent FR-2,586, 913, the disclosure of which is incorporated herein by reference.

The examples which follow are intended to illustrate the invention without, however, limiting the scope thereof.

EXAMPLES

The following dye compositions 1(A) to 4(A) in accordance with the invention were prepared (contents in grams):

| COMPOSITION | 1 (A) | 2 (A) | 3 (A) | 4 (A) |
| --- | --- | --- | --- | --- |
| Para-phenylenediamine | 0.324 | | | |
| Para-toluylenediamine dihydrochloride | | 0.585 | | |
| 2,6-Dimethyl-para-phenylenediamine dihydrochloride | | | 0.627 | |
| 2-β-Hydroxyethyl-para-phenylenediamine dihydrochloride | | | | 0.675 |
| 6-Hydroxyindoline | 0.515 | 0.515 | 0.515 | 0.515 |

-continued

| | | | | |
|---|---|---|---|---|
| hydrochloride | | | | |
| Common dye support (*) | (*) | (*) | (*) | (*) |
| Water qs | 100 g | 100 g | 100 g | 100 g |

(*) common dye support:

| | |
|---|---|
| Oleyl alcohol polyglycerolated with 2 mol of glycerol | 4.0 g |
| Oleyl alcohol polyglycerolated with 4 mol of glycerol, containing 78% of active material (AM) | 5.69 g AM |
| Oleic acid | 3.0 g |
| Oleylamine containing 2 mol of ethylene oxide, sold under the trade name Ethomeen O12 by the company AKZO | 7.0 g |
| Diethylaminopropyl laurylaminosuccinamate, sodium salt, containing 55% of AM | 3.0 g AM |
| Oleyl alcohol | 5.0 g |
| Oleic acid diethanolamide | 12.0 g |
| Propylene glycol | 3.5 g |
| Ethyl alcohol | 7.0 g |
| Dipropylene glycol | 0.5 g |
| Propylene glycol monomethyl ether | 9.0 g |
| Sodium metabisulphite in aqueous solution containing 35% of AM | 0.455 g AM |
| Ammonium acetate | 0.8 g |
| Antioxidant, sequestering agent | qs |
| Fragrance, preserving agent | qs |
| Monoethanolamine qs | pH 9.8 |

At the time of use, each dye composition 1(A) to 4(A) was mixed with an equal amount by weight of an oxidizing composition (B) containing 20-volumes aqueous hydrogen peroxide solution (6% by weight), the pH of which had been adjusted to between 1 and 1.5 with 2.5 g of orthophosphoric acid per 100 g of aqueous hydrogen peroxide solution.

Each resulting composition had a pH of less than 7, and was applied for 30 minutes to locks of natural grey hair containing 90% white hairs. The locks of hair were then rinsed, washed with a standard shampoo and then dried.

Compositions 1'(A) to 4'(A) were also prepared. These compositions 1'(A) to 4'(A) differed from the compositions 1(A) to 4(A) only in that the monoethanolamine used to adjust the pH of the dye composition (see the common dye support defined above) was replaced by 10 g of aqueous ammonia containing 20% of $NH_3$.

At the time of use, each dye composition 1'(A) to 4'(A) was mixed with an equal amount by weight of an oxidizing composition (B) containing 20-volumes aqueous hydrogen peroxide solution (6% by weight) of pH 3.

Each resulting composition (not forming part of the invention) had a pH of greater than 7, and was applied for 30 minutes to locks of natural grey hair containing 90% white hairs. The locks of hair were then rinsed, washed with a standard shampoo and then dried.

The color of the locks was then evaluated in the Munsell system using a Minolta CM 2002 colorimeter.

According to the Munsell notation, a color is defined by the expression H V/C in which the three parameters respectively denote the shade or Hue (H), the intensity or Value (V) and the purity or Chromaticity (C), the oblique line in this expression simply being a convention and not indicating a ratio.

The difference between the color of the locks before and after the dyeing was calculated by applying the Nickerson formula:

$$\Delta E = 0.4 C_0 \Delta H + 6 \Delta V + 3 \Delta C$$

as described, for example, in "Couleur, Industrie et Technique"; pages 14–17; vol. No. 5; 1978.

In this formula, $\Delta E$ represents the difference in color between two locks, $\Delta H$, $\Delta V$ and $\Delta C$ represent the variation in absolute value of the parameters H, V and C, and $C_0$ represents the purity of the lock relative to which it is desired to evaluate the color difference.

$\Delta E$ thus reflects the power of the coloration obtained, which is greater the higher the value of $\Delta E$.

The color of the locks before dyeing was: 3.4 Y 5.7/1.6 and thus $C_0 = 1.6$.

The results are given in the table below:

| EXAMPLE [COMPOSITION] | pH OF THE MIXTURE APPLIED TO THE HAIR | COLOUR OF THE LOCK AFTER DYEING | POWER OF THE COLORATION | | | |
|---|---|---|---|---|---|---|
| | | | ΔH | ΔV | ΔC | ΔE |
| 1[1 (A)] | 6.9 | 9.8 RP 2.4/0.8 | 23.6 | 3.3 | 0.8 | 37.3 |
| 1'[1'(A)] | 9.9 | 1,2 YR 3.3/1.4 | 12.2 | 2.4 | 0.2 | 22.8 |
| 2 [2(A)] | 6.8 | 7.9 RP 2.6/1.0 | 25.5 | 3.1 | 0.6 | 36.7 |
| 2'[2'(A)] | 9.8 | 8.1 R 3.2/1.3 | 15.3 | 2.5 | 0.3 | 25.7 |
| 3[3(A)] | 6.8 | 2.8 RP 2.7/1.0 | 30.6 | 3.0 | 0.6 | 39.4 |
| 3'[3'(A)] | 9.8 | 3.2 R 3.2/1.2 | 20.2 | 2.5 | 0.4 | 29.1 |
| 4[4(A)] | 6.7 | 9.7 RP 3.0/1.2 | 23.7 | 2.7 | 0.4 | 32.6 |
| 4'[4'(A)] | 9.8 | 0.8 YR 3.6/1.4 | 12.6 | 2.1 | 0.2 | 21.3 |

These results clearly show that when the dyeing is performed with the ready-to-use dye compositions in accordance with the invention, that is to say compositions in which the pH is less than 7 (ready-to-use dye compositions of Examples 1 to 4), it leads to more powerful colorations than those obtained with the ready-to-use dye compositions not forming part of the invention (ready-to-use dye compositions of Examples 1' to 4'), which effectively have a pH of greater than 7.

What is claimed is:

1. A ready-to-apply composition for the oxidation dyeing of keratin fibres, which composition comprises, in a medium which is suitable for dyeing:
    an effective amount to dye said keratin fibres of at least one oxidation base selected from para-phenylenediamines, bis(phenyl)alkylenediamines, para-aminophenols, ortho-aminophenols, heterocyclic bases and the acid addition salts of said oxidation bases,
    an effective amount to dye said keratin fibres of at least one coupler selected from 6-hydroxyindoline and acid addition salts of said compound, and
    at least one oxidizing agent,
    wherein the pH of said ready-to-apply composition is less than 7.

2. A composition according to claim 1, wherein said para-phenylenediamines are selected from compounds corresponding to formula (I) and the acid addition salts of said compounds:

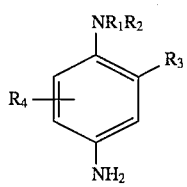

(I)

in which:

R₁ represents a hydrogen atom or a $C_1$–$C_4$ alkyl, $C_1$–$C_4$ monohydroxyalkyl, $C_2$–$C_4$ polyhydroxyalkyl, ($C_1$–$C_4$)alkoxy($C_1$–$C_4$)alkyl, phenyl or 4'-aminophenyl radical, R₂ represents a hydrogen atom or a $C_1$–$C_4$ alkyl, $C_1$–$C_4$ monohydroxyalkyl or $C_2$–$C_4$ polyhydroxyalkyl radical, R₃ represents a hydrogen atom, a halogen atom such as a chlorine, bromine, iodine or fluorine atom, or a $C_1$–$C_4$ alkyl, $C_1$–$C_4$ monohydroxyalkyl or $C_1$–$C_4$ hydroxyalkoxy radical, and R₄ represents a hydrogen atom or a $C_1$–$C_4$ alkyl radical.

3. A composition according to claim 2, wherein said para-phenylenediamines of formula (I) are selected from para-phenylenediamine, para-toluylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-amino-N,N-bis(β-hydroxyethyl)-3-mehtylaniline, 4-amino-3-chloro-N,N-bis(β-hydroxyethyl)aniline, 4-amino-N-(β-methoxyethyl)aniline, 2-β-hydroxyethyl-para-phenylenediamine, 2-fluoro-para-phenylenediamine, 2-isopropyl-para-phenylenediamine, 2-n-propyl-para-phenylenediamine, N-(β-hydroxypropyl)-para-phenylenediamine, 2-hydroxymethyl-para-phenylenediamine, N,N-dimethyl-3-methyl-para-phenylenediamine, N-(ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine and the acid addition salts of said compounds.

4. A composition according to claim 3, wherein said para-phenylenediamines of formula (I) are selected from para-phenylenediamine, para-toluylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 4-amino-N-(β-methoxyethyl)aniline, 2-chloro-para-phenylenediamine and the acid addition salts of said compounds.

5. A composition according to claim 1, wherein said bis(phenyl)alkylenediamines are selected from compounds of formula (II) and the acid addition salts of said compounds:

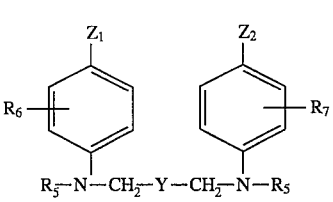

(II)

in which:

Z₁ and Z₂, which may be identical or different, represent a hydroxyl radical or a NHR₈ radical in which R₈ represents a hydrogen atom or a $C_1$–$C_4$ alkyl radical, R₅ independently represents a hydrogen atom or a $C_1$–$C_4$ alkyl, $C_1$–$C_4$ monohydroxyalkyl or $C_2$–$C_4$ polyhydroxyalkyl radical or a $C_1$–$C_4$ aminoalkyl radical in which the amino residue may be substituted, R₆ and R₇, which may be identical or different, represent a hydrogen or halogen atom or a $C_1$–$C_4$ alkyl radical, Y represents a radical, the radical being
—(CH₂)ₙ—; —(CH₂)ₘ—O—(CH₂)ₘ—; —(CH₂)ₘ—CHOH—(CH₂)ₘ— or

—(CH₂)ₘ—N—(CH₂)ₘ—;
         |
         CH₃ in which n is an integer ranging from 0 to 8 inclusively and m is independently an integer ranging from 0 to 4 inclusively.

6. A composition according to claim 5, wherein said bis(phenyl)alkylenediamines are selected from N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine and N,N'-bis(ethyl)-N,N'-bis(4'-amino-3'-methylphenyl)ethylenediamine and the acid addition salts of said compounds.

7. A composition according to claim 6, wherein said bis(phenyl)alkylenediamines are selected from N,N'-bis(β-hydroxyethyl)-N,N'-bis(4'-aminophenyl)-1,3-diaminopropanol and the acid addition salts of said compound.

8. A composition according to claim 1, wherein said para-aminophenols are selected from compounds of formula (III) and the acid addition salts of said compounds:

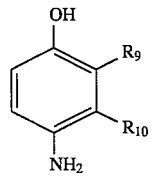

(III)

in which:

R₉ represents a hydrogen atom or a $C_1$–$C_4$ alkyl, $C_1$–$C_4$ monohydroxyalkyl, ($C_1$–$C_4$)alkoxy($C_1$–$C_4$)alkyl or $C_1$–$C_4$ aminoalkyl radical, R₁₀ represents a hydrogen or fluorine atom or a $C_1$–$C_4$ alkyl, $C_1$–$C_4$ monohydroxyalkyl, $C_2$–$C_4$ polyhydroxyalkyl, $C_1$–$C_4$ aminoalkyl, $C_1$–$C_4$ cyanoalkyl or ($C_1$–$C_4$)alkoxy($C_1$–$C_4$)alkyl radical;

it being understood that at least one of said radicals R₉ or R₁₀ represents a hydrogen atom.

9. A composition according to claim 8, wherein said para-aminophenols are selected from para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol and 4-amino-2-(β-hydroxyethyl-aminomethyl)phenol and the acid addition salts of said compounds.

10. A composition according to claim 1, wherein said ortho-aminophenols are selected from 2-aminophenol, 2-amino-5-methylphenol, 2-amino-6-methylphenol, 5-acetamido-2-aminophenol and the acid addition salts of said compounds.

11. A composition according to claim 1, wherein said heterocyclic bases are selected from pyridine derivatives, pyrimidine derivatives, pyrazole derivatives and the acid addition salts of said compounds.

12. A composition according to claim 11, wherein said heterocyclic bases are selected from 2,4,5,6-tetraaminopyrimidine, 2,5-diaminopyridine, 4,5-diamino-1-methylpyrazole, 3,4-diaminopyrazole, 4-hydroxy-2,5,6-triaminopyrimidine and the acid addition salts of said compounds.

13. A composition according to claim 1, wherein said acid addition salts are selected from hydrochlorides, hydrobromides, sulphates and tartrates.

14. A composition according to claim 1, wherein said at least one oxidation base represents from 0.0005 to 12% by weight relative to the total weight of the dye composition.

15. A composition according to claim 14, wherein said at least one oxidation base represents from 0.005 to 6% by weight relative to the total weight of the dye composition.

16. A composition according to claim 1, wherein said at least one coupler represents from 0.0005 to 5% by weight relative to the total weight of the dye composition.

17. A composition according to claim 16, wherein said at least one coupler represents from 0.005 to 3% by weight relative to the total weight of the dye composition.

18. A composition according to claim 1, which composition has a pH ranging from 3 to 6.9.

19. A composition according to claim 1, wherein said at least one oxidizing agent is selected from hydrogen peroxide, urea peroxide, alkali metal bromates and persalts.

20. A composition according to claim 19, wherein said persalts are perborates or persulphates.

21. A process for the oxidation dyeing of keratin fibres, comprising the step of applying to said fibres an effective amount to dye said fibres of a ready-to-apply composition for the oxidation dyeing of keratin fibres according to claim 1.

22. A process for dyeing keratin fibres comprising the steps of:

separately storing a composition (A) which comprises, in a medium which is suitable for dyeing, an effective amount to dye said keratin fibres of at least one oxidation base selected from para-phenylenediamines, bis(phenyl)alkylenediamines, para-aminophenols, ortho-aminophenols, heterocyclic bases and the acid addition salts of said oxidation bases, and an effective amount to dye said keratin fibres of at least one coupler selected from 6-hydroxyindoline and acid addition salts thereof, and a composition (B) which comprises, in a medium which is suitable for dyeing, at least one oxidizing agent which is selected from hydrogen peroxide, urea peroxide, alkali metal bromates and persalts;

mixing, before application to said keratin fibres, from 10 to 90% of composition (A) and from 90 to 10% of the composition (B), said resultant mixture having a pH less than 7; and then applying said mixture of compositions (A) and (B) to said keratin fibres.

23. A multi-compartment device or dyeing kit, which comprises at least two compartments, wherein a first compartment contains said composition (A) as defined in claim 22 and a second compartment contains said composition (B) as defined in claim 22.

24. A composition according to claim 1, wherein said medium suitable for dyeing comprises water or a mixture of water and at least one organic solvent selected from $C_1$–$C_4$ lower alkanols, glycerol, glycols and glycol ethers, aromatic alcohols and mixtures thereof.

* * * * *

UNITED STATES PATENT AND TRADEMARK OFFICE
CERTIFICATE OF CORRECTION

PATENT NO. : 5,620,484
DATED : April 15, 1997
INVENTOR(S) : Mireille MAUBRU

It is certified that error appears in the above-indentified patent and that said Letters Patent is hereby corrected as shown below:

In the Claims, claim 3, column 9, line 36, "N,N-bis($\beta$-hydroxyethyl)-3-mehtylaniline" should read --N,N-bis($\beta$-hydroxyethyl)-3-methylaniline--.

Signed and Sealed this

Twelfth Day of August, 1997

Attest:

BRUCE LEHMAN

Attesting Officer  Commissioner of Patents and Trademarks